(12) United States Patent
Jones et al.

(10) Patent No.: US 11,482,873 B2
(45) Date of Patent: Oct. 25, 2022

(54) VAPORIZER CHARGING STRUCTURE

(71) Applicant: CANOPY GROWTH CORPORATION, Smiths Falls (CA)

(72) Inventors: Mark Jones, Toronto (CA); Andrew Stewart, Ottawa (CA); Yan Vermette, Ottawa (CA)

(73) Assignee: CANOPY GROWTH CORPORATION, Smiths Falls (CA)

( * ) Notice: Subject to any disclaimer, the term of this patent is extended or adjusted under 35 U.S.C. 154(b) by 0 days.

(21) Appl. No.: 17/223,160

(22) Filed: Apr. 6, 2021

(65) Prior Publication Data

US 2021/0226461 A1 Jul. 22, 2021

Related U.S. Application Data

(63) Continuation of application No. 17/123,371, filed on Dec. 16, 2020, now Pat. No. 10,998,744, which is a continuation of application No. PCT/CA2020/051361, filed on Oct. 9, 2020.

(60) Provisional application No. 62/915,141, filed on Oct. 15, 2019.

(51) Int. Cl.
| | | |
|---|---|---|
| *A24F 40/40* | (2020.01) | |
| *H02J 7/00* | (2006.01) | |
| *A24F 40/90* | (2020.01) | |
| *A61M 15/06* | (2006.01) | |

(52) U.S. Cl.
CPC ............ *H02J 7/0045* (2013.01); *A24F 40/40* (2020.01); *A24F 40/90* (2020.01); *H02J 7/0049* (2020.01); *A61M 15/06* (2013.01)

(58) Field of Classification Search
CPC .......... H02J 7/0045; A24F 40/90; A24F 40/40
See application file for complete search history.

(56) References Cited

U.S. PATENT DOCUMENTS

| | | |
|---|---|---|
| 5,878,752 A | 3/1999 | Adams et al. |
| 8,539,959 B1 | 9/2013 | Scatterday |
| 9,032,968 B2 | 5/2015 | Glasberg et al. |
| 9,131,733 B2 | 9/2015 | Liu |
| 9,277,769 B2 | 3/2016 | Liu |

(Continued)

FOREIGN PATENT DOCUMENTS

| | | |
|---|---|---|
| CN | 108497559 A | 5/2018 |
| EP | 2022349 A1 | 2/2009 |

(Continued)

OTHER PUBLICATIONS

International Search Report and Written Opinion dated Dec. 23, 2020 for related application PCT/CA2020/051361 (12 pgs).

*Primary Examiner* — Neil Abrams
(74) *Attorney, Agent, or Firm* — Stinson LLP

(57) ABSTRACT

A charging structure for a vaporizer. The charging structure includes a housing, a first electrical contact coupled to and extending outward from a first end of the housing, a spacer coupled to the first electrical contact, and a second electrical contact coupled to and extending outward from the spacer. The first electrical contact includes an exposed outer surface that extends in a continuous loop. The second electrical contact includes an exposed side surface that extends in a continuous loop and an end surface coupled to the side surface. Both the side surface and the end surface are electrically conductive. A vaporizer including the charging structure.

21 Claims, 11 Drawing Sheets

(56) References Cited

U.S. PATENT DOCUMENTS

| | | | |
|---|---|---|---|
| 9,642,396 B2 * | 5/2017 | Liu | .................... H01M 50/213 |
| 9,901,116 B2 * | 2/2018 | Liu | ........................ A24F 40/60 |
| 10,010,114 B2 | 7/2018 | Jordan et al. | |
| 10,215,390 B2 | 2/2019 | Maglica et al. | |
| 10,218,193 B2 | 2/2019 | Gratton | |
| 10,998,744 B1 * | 5/2021 | Jones | ..................... A24F 40/40 |
| 11,134,722 B2 * | 10/2021 | Verleur | .................. A24F 40/00 |
| 2006/0232239 A1 | 10/2006 | Maglica et al. | |
| 2011/0277780 A1 | 11/2011 | Terry et al. | |
| 2016/0286857 A1 | 10/2016 | Liu | |
| 2016/0331029 A1 | 11/2016 | Contreras | |
| 2017/0245554 A1 | 8/2017 | Perez et al. | |
| 2018/0248393 A1 | 8/2018 | Sun et al. | |
| 2019/0000146 A1 | 1/2019 | Lin et al. | |

FOREIGN PATENT DOCUMENTS

| | | |
|---|---|---|
| WO | WO 2013/093695 A1 | 6/2013 |
| WO | WO 2015/058367 A1 | 4/2015 |
| WO | WO 2019/037883 A1 | 2/2019 |

* cited by examiner

VAPORIZER CHARGING STRUCTURE

CROSS-REFERENCE TO RELATED APPLICATIONS

This application claims priority to and is a Continuation of U.S. patent application Ser. No. 17/123,371 filed on Dec. 16, 2020 which is a Continuation of International Application PCT/CA2020/051361 filed on Oct. 9, 2020, which is based on and claims priority to U.S. Provisional Application Ser. No. 62/915,141 filed on Oct. 15, 2019, all of which are incorporated herein by reference in their entirety.

BACKGROUND OF THE INVENTION

1. Field of the Invention

The invention is directed toward a vaporizer and, in particular, to a charging structure for a vaporizer.

2. Description of Related Art

There are different types of vaporizers designed for the personal consumption of tobacco products, as well as cannabis for medical and recreational purposes. Conventional vaporizers typically include a battery, a heater, and a reservoir or holder containing a substance for vaporization by the heater. The battery may be located in a reusable base of the vaporizer, and the heater and reservoir may be located in a disposable cartridge that may be connected to the base. Many types of vaporizers have a rechargeable battery. One type of vaporizer with a rechargeable battery has a base with a charging port that is configured for connection to a charging cable. Another type of vaporizer with a rechargeable battery has a base and a cartridge that connect with an electromechanical connection commonly referred to as a "510" threaded connection. To charge the battery, the cartridge is typically unscrewed from the base and a charger is screwed on to the base using the "510" threaded connection. Thus, the cartridge must be removed from the base prior to charging. Other conventional vaporizers have electrical contacts positioned on an exterior surface of the vaporizer so that the vaporizer may be recharged without removing the cartridge from the base. These vaporizers, however, are structured so that they are difficult to assemble. Further, the electrical contacts must be precisely positioned on a charger in order for the charger to recharge the battery.

BRIEF SUMMARY OF THE INVENTION

One exemplary embodiment of the invention described herein is directed toward a charging structure for a vaporizer. The charging structure includes a housing, a first electrical contact coupled to and extending outward from a first end of the housing, a spacer coupled to the first electrical contact, and a second electrical contact coupled to and extending outward from the spacer. The first electrical contact includes an exposed outer surface that extends in a continuous loop. The second electrical contact includes an exposed side surface that extends in a continuous loop, and an end surface coupled to the side surface. Both the side surface and the end surface are electrically conductive.

In some embodiments, the charging structure may include a light source positioned in an interior cavity defined by at least one of the housing, the first electrical contact, the spacer, and the second electrical contact. The spacer may be translucent or transparent, and the light source may be positioned so that light emitted from the light source is visible at an outer surface of the spacer.

In some embodiments, the exposed outer surface of the first electrical contact and the exposed side surface of the second electrical contact are each cylindrical.

In some embodiments, the exposed side surface of the second electrical contact is integrally formed with the end surface.

In some embodiments, the first electrical contact includes a coupling section that engages an inner surface of the housing, the spacer includes a proximal section that engages an inner surface of the first electrical contact, and the spacer includes a distal section that engages an inner surface of the second electrical contact.

In some embodiments, the exposed outer surface of the first electrical contact includes a proximal end adjacent the first end of the housing and a distal end, the spacer includes a second exposed outer surface with a proximal end adjacent the distal end of the exposed outer surface of the first electrical contact and a distal end, and the exposed side surface of the second electrical contact includes a proximal end adjacent the distal end of the second exposed outer surface of the spacer and a distal end. The exposed outer surface of the first electrical contact, the second exposed outer surface of the spacer, and the exposed side surface of the second electrical contact may be substantially flush with an outer surface of the housing. The housing may define an opening at the first end, and the first electrical contact may include a coupling section that extends from the proximal end of the exposed outer surface through the opening. The first electrical contact may define a second opening at the distal end of the first electrical contact, the spacer may include a proximal section that extends from the proximal end of the second exposed outer surface through the second opening, and the spacer may include a distal section that extends from the distal end of the second exposed outer surface toward the end surface of the second electrical contact. The distal section of the spacer may define a third opening, and the end surface of the second electrical contact may substantially block the third opening. The proximal section of the spacer may engage a first inner surface of the first electrical contact, and the distal section of the spacer may engage a second inner surface of the second electrical contact.

In some embodiments, the charging structure includes a battery that is electrically coupled to the first electrical contact and to the second electrical contact.

In some embodiments, an electromechanical connector is positioned at the second end of the housing. The electromechanical connector includes a positive electrical terminal that is electrically coupled to the battery and a negative electrical terminal that is electrically coupled to the battery.

Another exemplary embodiment of the invention described herein is directed toward a vaporizer having the charging structure described above.

The charging structure may be configured for use with a charger having two electrical contacts that are spaced apart in the same manner as the first and second electrical contacts of the charging structure. One electrical contact of the charger may be configured to contact the side and/or end surface of the second electrical contact of the charging structure. The charger may include a receptacle configured to receive the charging structure. The charging structure may be incorporated into a base of a vaporizer, and the base may be configured for connection to a cartridge. The charging structure may charge a battery in the base without disconnecting the cartridge from the base.

Another exemplary embodiment of the invention described herein is directed toward a charging structure for a vaporizer. The charging structure includes a housing with first and second ends. A first electrical contact is coupled to and extends outward from the first end of the housing. The first electrical contact has an exposed side surface that extends in a continuous loop. A second electrical contact is coupled to the second end of the housing. The second electrical contact comprises an exposed outer surface that extends in a continuous loop.

In some embodiments of the exemplary embodiment described above, the first electrical contact may include an end surface coupled to the side surface, wherein both the side surface and the end surface are electrically conductive. The exposed side surface of the first electrical contact may be integrally formed with the end surface.

In some embodiments of the exemplary embodiment described above, a spacer may be coupled to the housing and the first electrical contact, the spacer positioned between the housing and the first electrical contact.

In some embodiments of the exemplary embodiment described above, the exposed side surface of the first electrical contact and the exposed outer surface of the second electrical contact may each be cylindrical.

In some embodiments of the exemplary embodiment described above, the exposed side surface of the first electrical contact, and the exposed outer surface of the second electrical contact may each be substantially flush with an outer surface of the housing.

In some embodiments of the exemplary embodiment described above, a battery may be electrically coupled to the first electrical contact and to the second electrical contact. An electromechanical connector may be positioned at the second end of the housing, the electromechanical connector having a positive electrical terminal that is electrically coupled to the battery and a negative electrical terminal that is electrically coupled to the battery. The second electrical contact may be positioned between the housing and the electromechanical connector.

Another exemplary embodiment of the invention described herein is directed toward a charging structure for a vaporizer. The charging structure includes a housing with first and second ends. At least a portion of the housing forms a first electrical contact. The first electrical contact has an exposed outer surface that extends in a continuous loop. A spacer is coupled to the first end of the housing. A second electrical contact is coupled to and extends outward from the spacer. The second electrical contact has an exposed side surface that extends in a continuous loop.

In some embodiments of the exemplary embodiment described above, the second electrical contact may have an end surface coupled to the side surface, wherein both the side surface and the end surface are electrically conductive. The exposed side surface of the second electrical contact may be integrally formed with the end surface.

In some embodiments of the exemplary embodiment described above, the exposed outer surface of the first electrical contact and the exposed side surface of the second electrical contact may each be cylindrical.

In some embodiments of the exemplary embodiment described above, the exposed outer surface of the first electrical contact may be substantially flush with the exposed side surface of the second electrical contact.

In some embodiments of the exemplary embodiment described above, a battery may be electrically coupled to the first electrical contact and to the second electrical contact. An electromechanical connector may be positioned at the second end of the housing, the electromechanical connector having a positive electrical terminal that is electrically coupled to the battery and a negative electrical terminal that is electrically coupled to the battery.

Additional aspects of the invention, together with the advantages and novel features appurtenant thereto, will be set forth in part in the description which follows, and in part will become apparent to those skilled in the art upon examination of the following, or may be learned from the practice of the invention. The objects and advantages of the invention may be realized and attained by means of the instrumentalities and combinations particularly pointed out in the appended claims.

DETAILED DESCRIPTION OF PREFERRED EMBODIMENT

Figure 1:
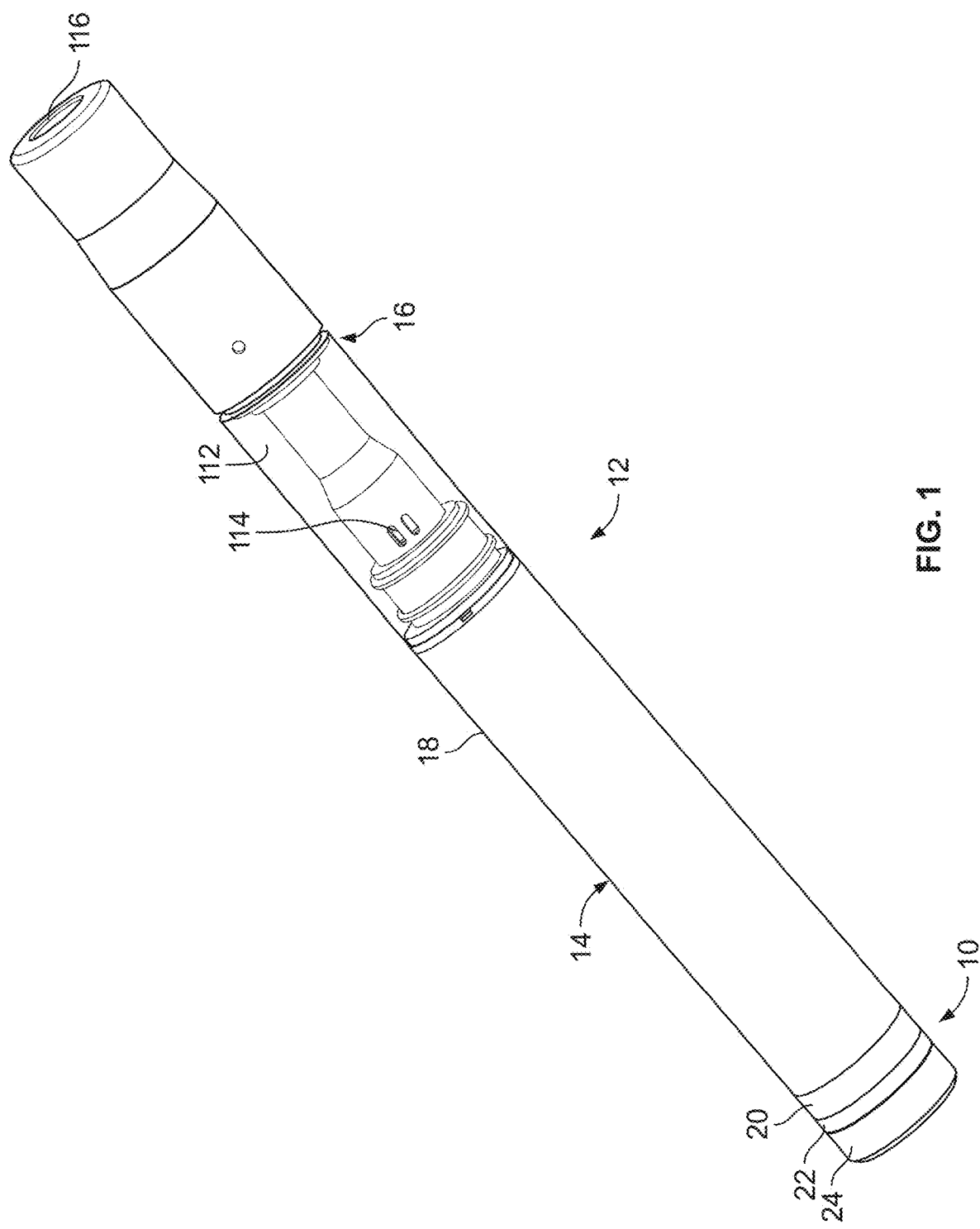
FIG. 1 is a perspective view of a vaporizer having a charging structure in accordance with the invention described herein.
Figure 2:
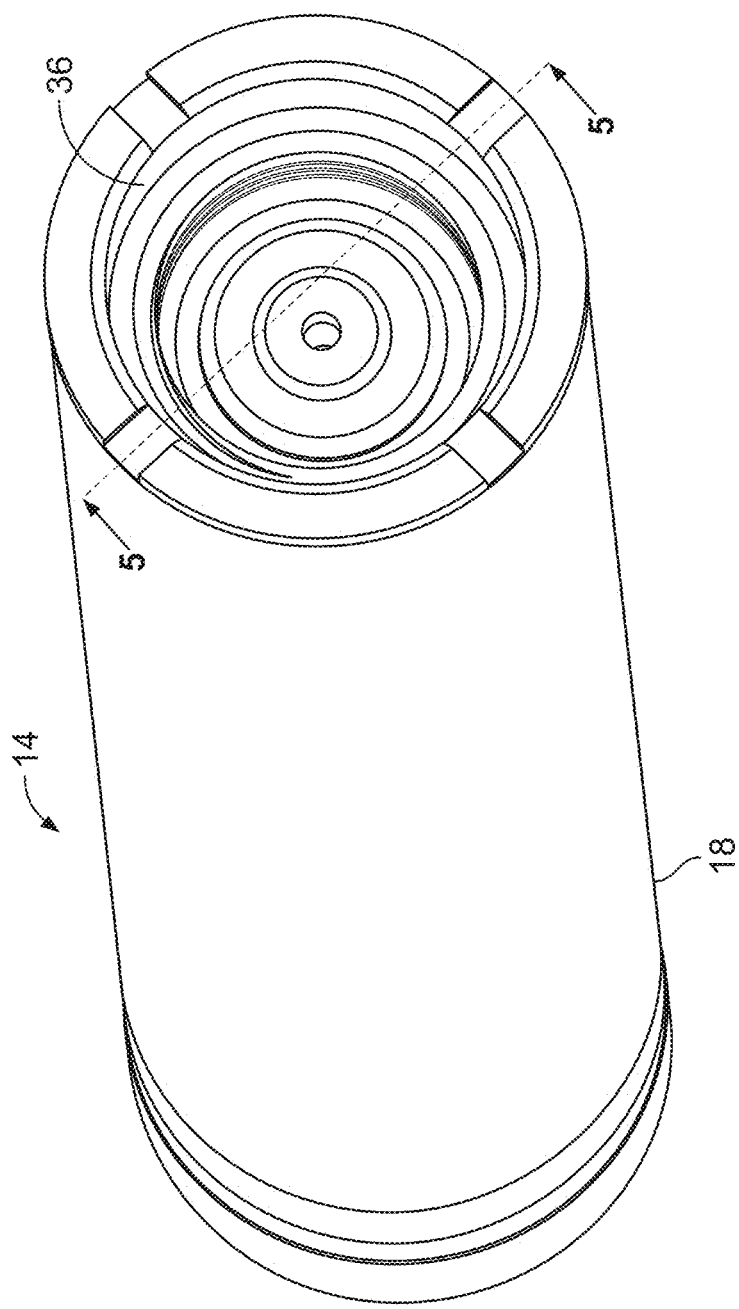
FIG. 2 is a perspective view of a base of the vaporizer shown in FIG. 1 showing an electromechanical connector configured for coupling the base to a cartridge of the vaporizer.
Figure 4:
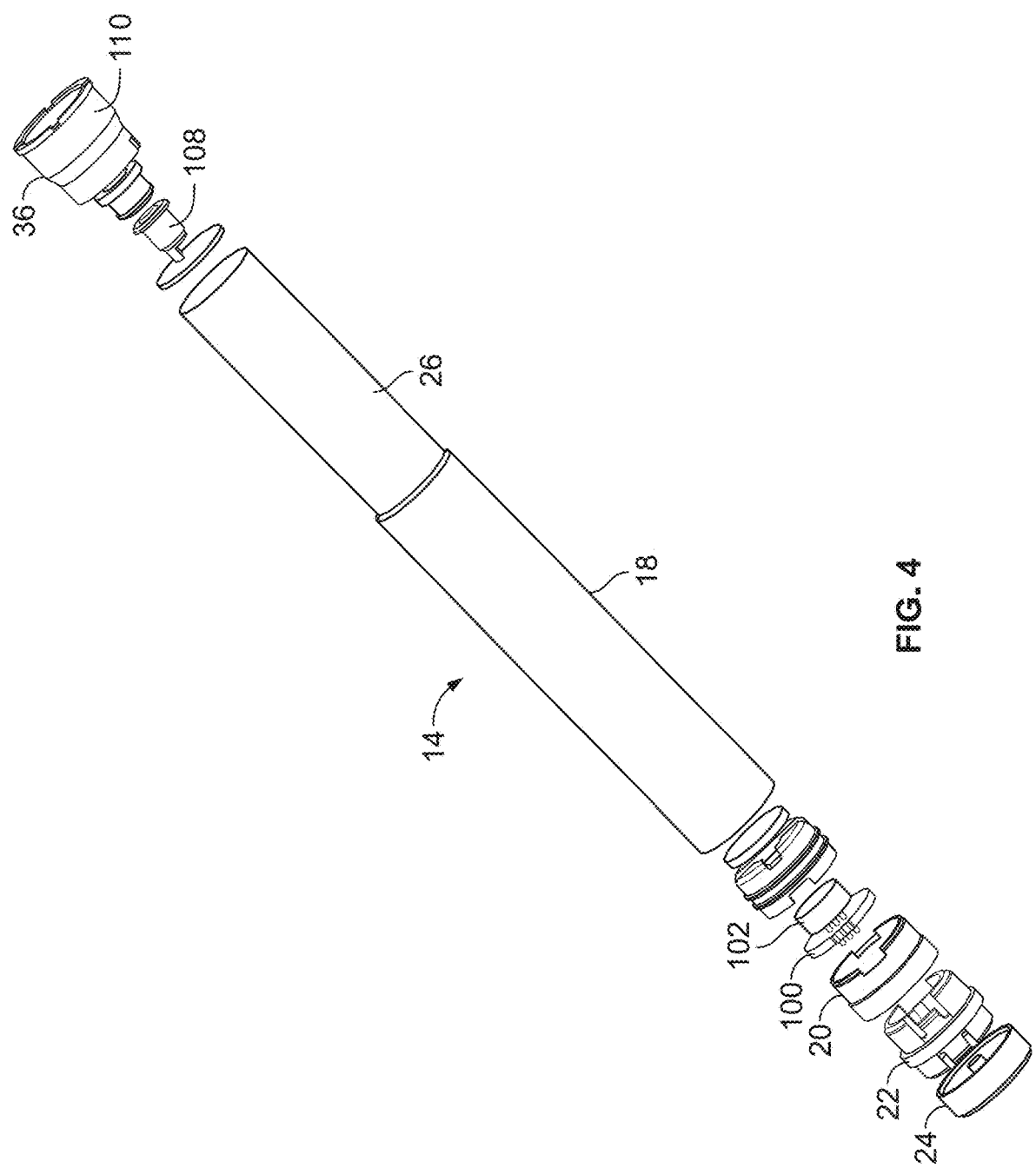
FIG. 4 is an exploded view of the base shown in FIG. 2.

A charging structure for a vaporizer in accordance with one exemplary embodiment of the invention described herein is identified generally as 10 in FIG. 1. The charging structure 10 may be used with any type of suitable vaporizer, including the vaporizer 12 shown in FIG. 1. Vaporizer 12 includes a base 14 and a cartridge 16 that is removably connected to the base 14. The charging structure 10 is formed as part of base 14 and includes a housing 18, a first electrical contact 20, a spacer 22, and a second electrical contact 24. As described in detail below, the charging structure 10 is configured for receiving electrical current to charge a battery 26 (FIGS. 4 and 5) housed within the base 14.

Figure 3:
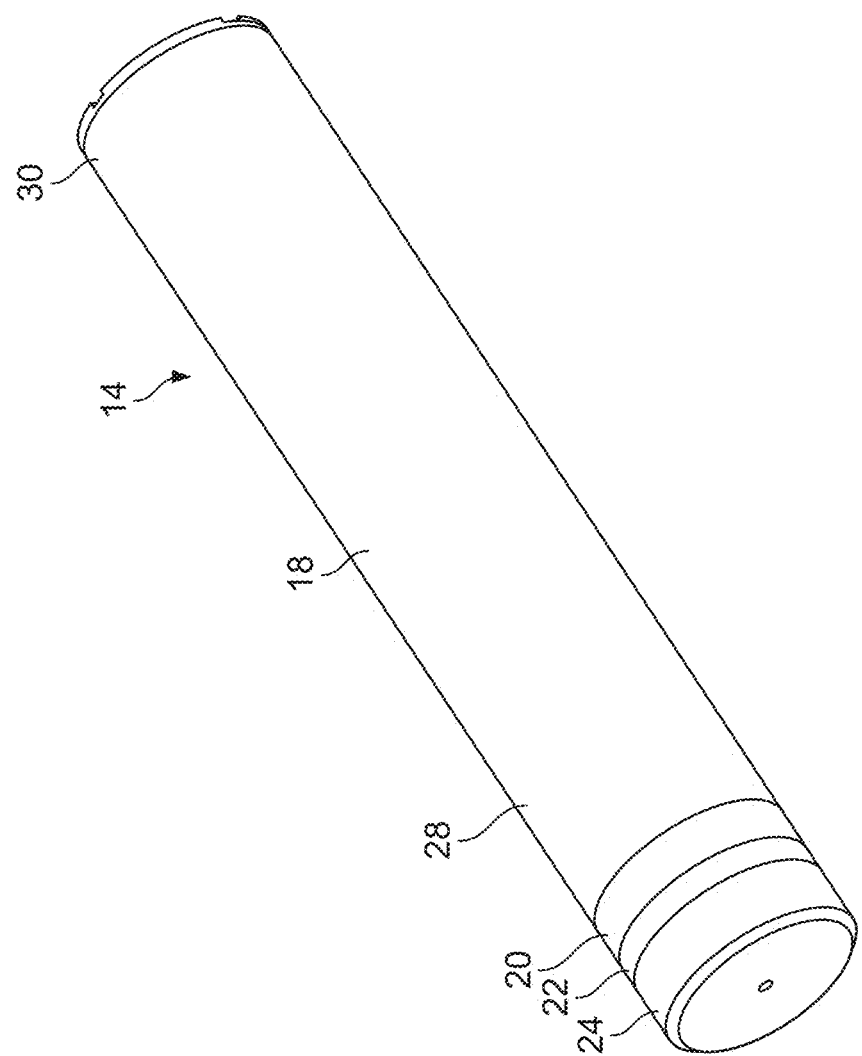
FIG. 3 is a perspective view of the base shown in FIG. 2 showing the charging structure.
Figure 5:
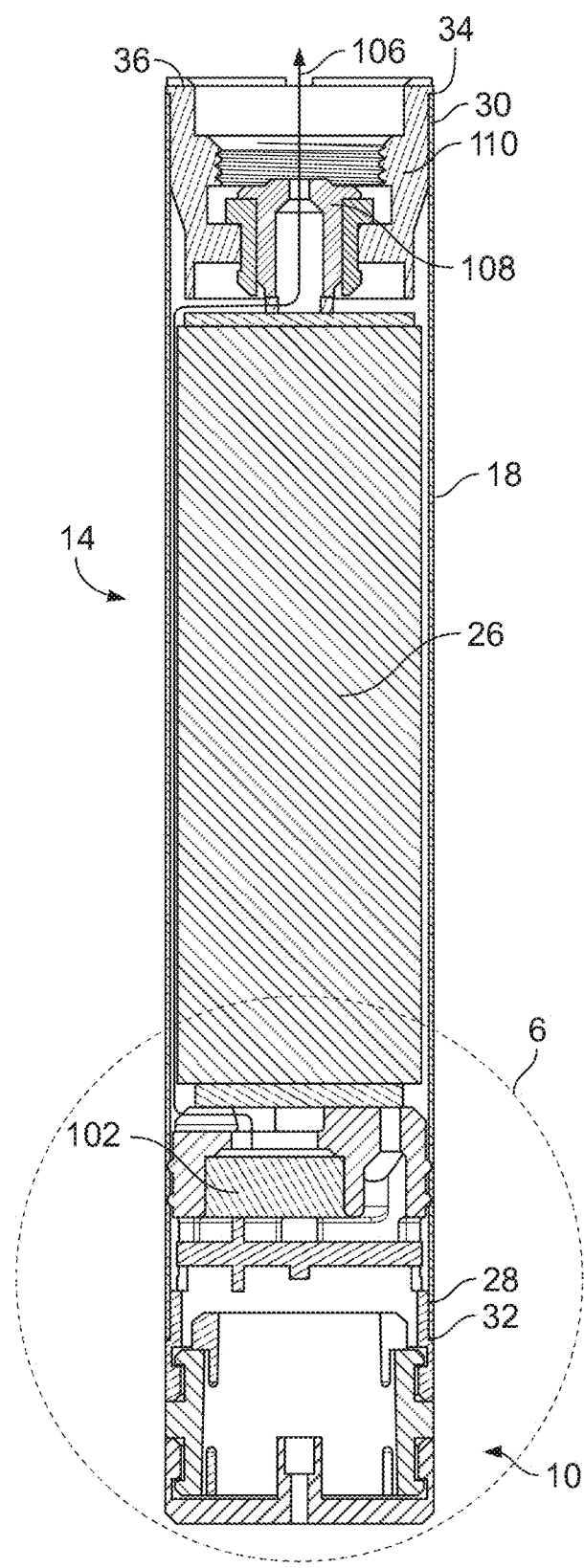
FIG. 5 is a cross-sectional view taken through the line 5-5 shown in FIG. 2.

Referring to FIG. 3, the housing 18 has a first end 28 and a second end 30. As shown in FIG. 5, the housing 18 is a generally cylindrical tube with a first opening 32 at the first end 28 and a second opening 34 at the second end 30.

Battery 26 is positioned within housing 18, and an electromechanical connector 36 is joined to the second end 30 of housing 18.

Figure 6:
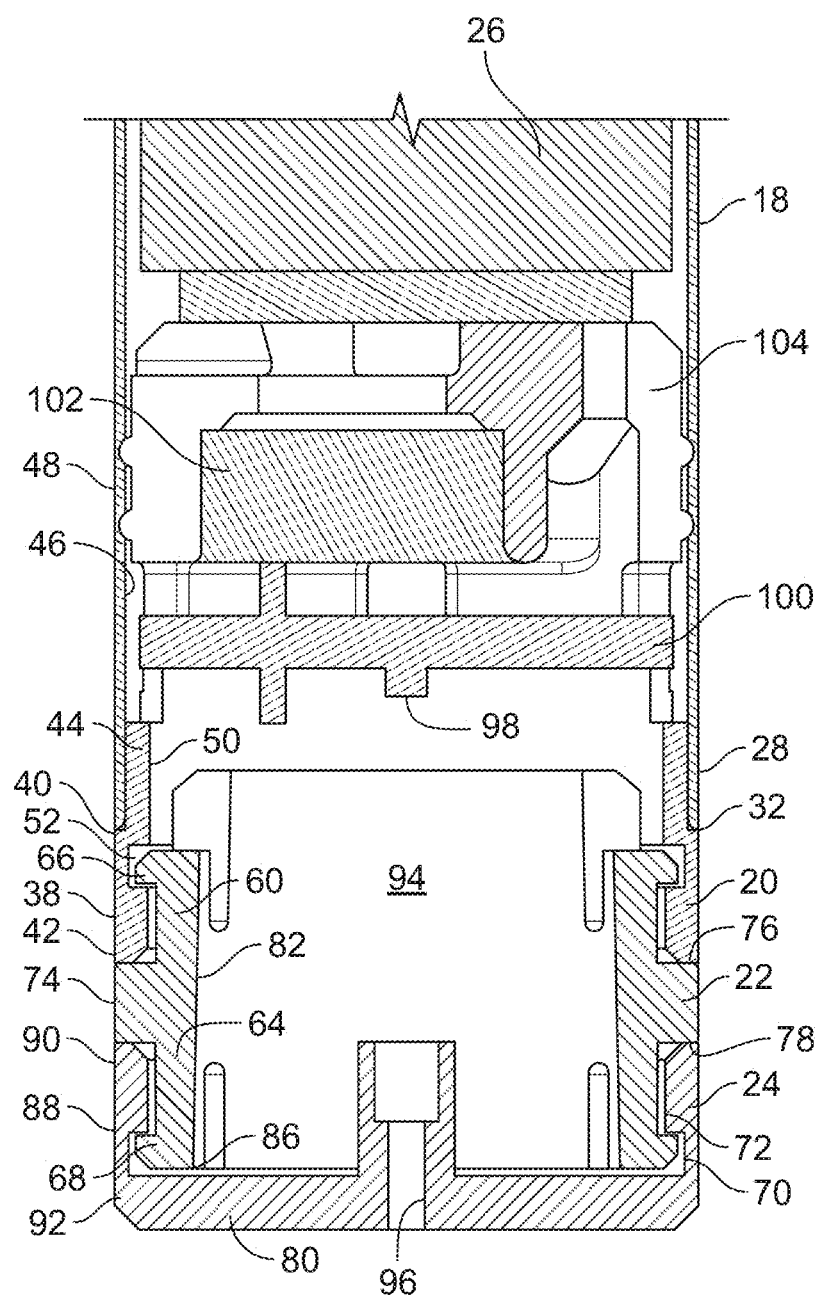
FIG. 6 is a detail view of the area 6 shown in FIG. 5 showing the charging structure.
Figure 7:
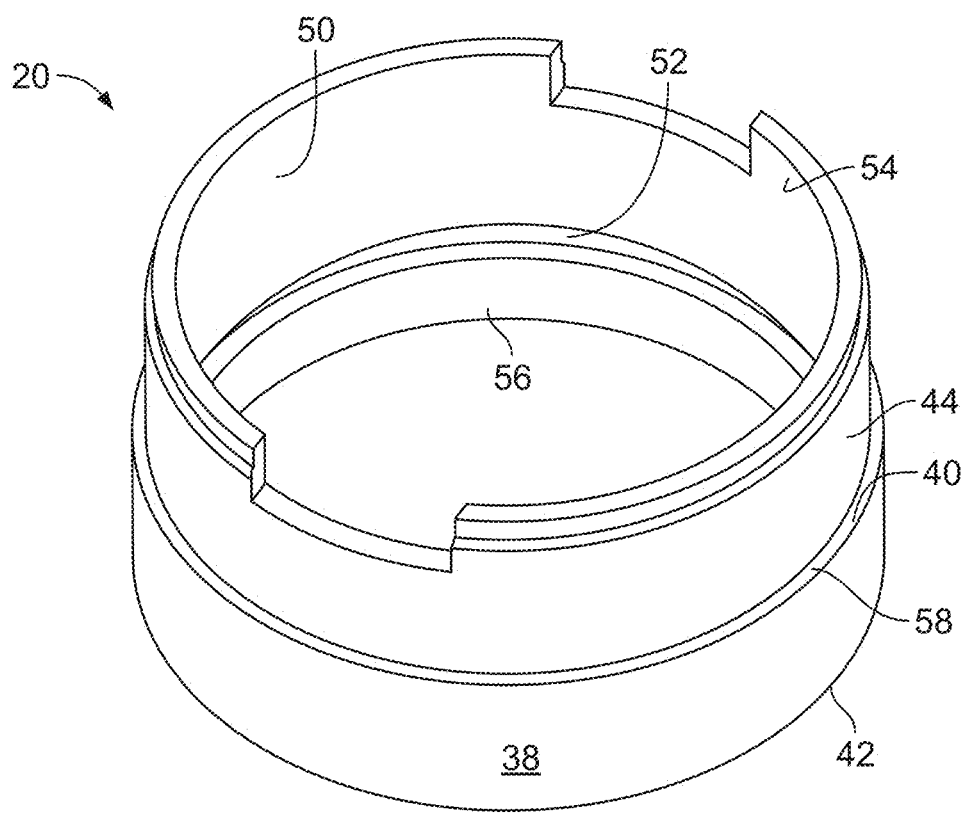
FIG. 7 is a perspective view of a first electrical contact of the charging structure shown in FIG. 3.

As best shown in FIG. 6, the first electrical contact 20 is coupled to the first end 28 of the housing 18. The first electrical contact 20 includes an exposed outer surface 38 that is cylindrical and extends in a continuous loop around the base 14. The exposed outer surface 38 has a proximal end 40 that is adjacent the first end 28 of the housing 18 and a distal end 42. A coupling section 44 extends from the proximal end 40 through the first opening 32 of the housing 18. The coupling section 44 engages an inner surface 46 of the housing 18 to join the first electrical contact 20 to the housing 18. The coupling section 44 may be joined to the housing 18 in any suitable manner including by a press-fit connection, a friction-fit connection, adhesive, brazing, and/or welding. Further, the coupling section 44 may include a clip that engages a slot on housing 18 or the housing 18 may include a clip that engages a slot on coupling section 44. The outer surface 38 is exposed in that it extends outward from the first end 28 of the housing 18 and is accessible from an exterior of the vaporizer 12. The outer surface 38 is generally flush with an outer surface 48 of the housing 18. An inner surface 50 of the first electrical contact 20 includes a recessed portion 52 that forms a slot around the inner surface 50. As shown in FIG. 7, the inner surface 50 defines a channel through the first electrical contact 20 with a first opening 54 and a second opening 56 at the distal end 42. The outer surface of the coupling section 44 is spaced radially inward from the exposed outer surface 38 to define a ledge 58 that abuts the first end 28 of housing 18. The first electrical contact 20 is formed from an electrically conductive material.

Figure 8:
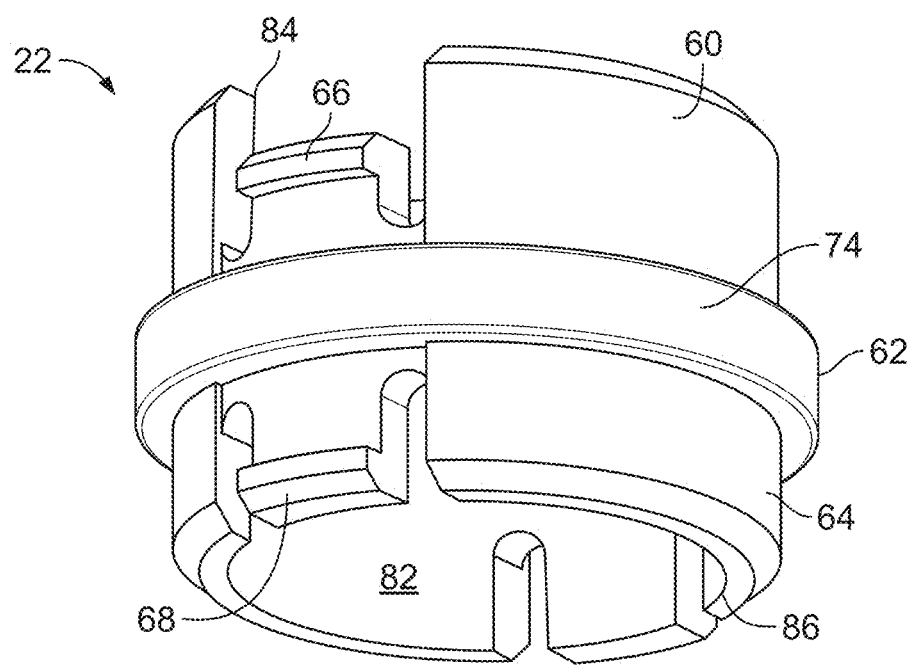
FIG. 8 is a perspective view of a spacer of the charging structure shown in FIG. 3.
Figure 9:
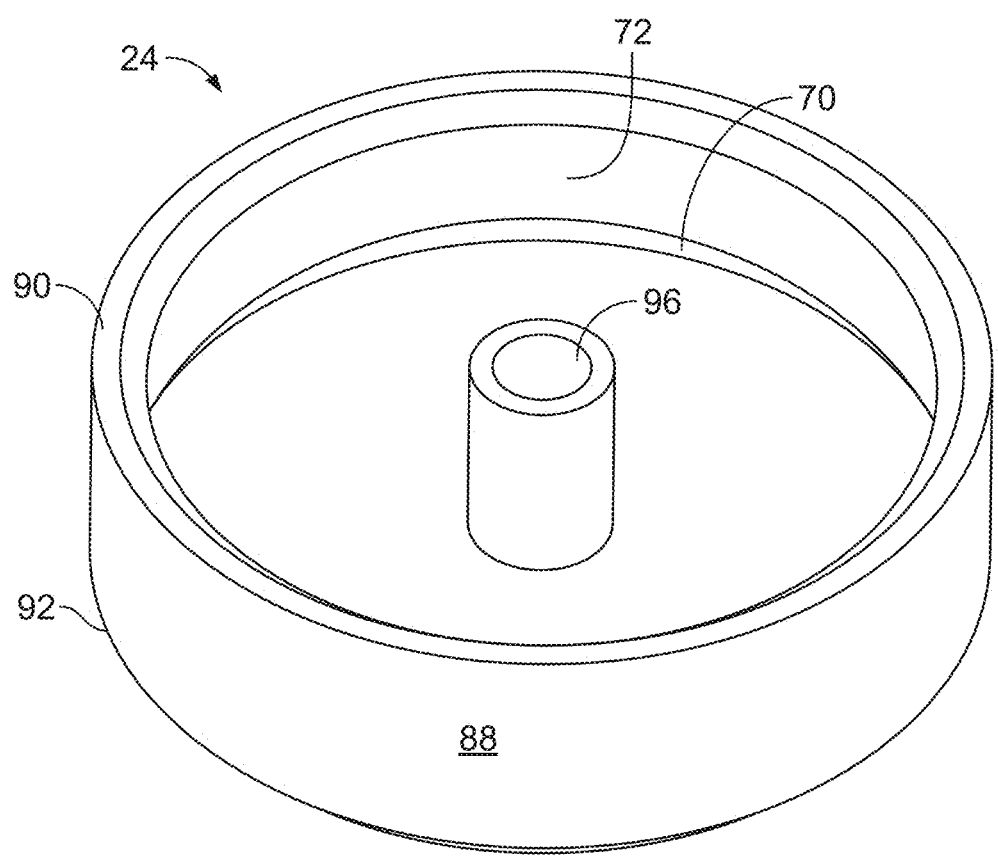
FIG. 9 is a perspective view of a second electrical contact of the charging structure shown in FIG. 3.

As shown in FIG. 6, the spacer 22 is coupled to and extends outward from the first electrical contact 20. Referring to FIG. 8, the spacer 22 includes a proximal section 60, a middle section 62, and a distal section 64. The proximal section 60 and distal section 64 are generally mirror images of each other on opposite ends of middle section 62. The proximal section 60 has two clips, one of which is identified as 66, positioned on opposite sides of spacer 22, and the distal section 64 has two clips, one of which is identified as 68, positioned on opposite sides of spacer 22. As shown in FIG. 6, clips 66 are positioned in the slot formed by recessed portion 52 to join spacer 22 to first electrical contact 20. Clips 68 are positioned in a slot formed by a recessed portion 70 of an inner surface 72 of second electrical contact 24 to join spacer 22 to second electrical contact 24. Thus, the proximal section 60 of the spacer 22 engages the inner surface 50 of the first electrical contact 20, and the distal section 64 of the spacer 22 engages the inner surface 72 of the second electrical contact 24. Spacer 22 serves to insulate first electrical contact 20 from second electrical contact 24 and is formed from an electrically insulating material. Alternatively, or in addition to using clips 66, the proximal section 60 of the spacer 22 may engage the inner surface 50 of the first electrical contact 20 in any suitable manner including by a press-fit connection, a friction-fit connection, or adhesive. Further, alternatively, or in addition to using clips 68, the distal section 64 of the spacer 22 may engage the inner surface 72 of the second electrical contact 24 in any suitable manner including by a press-fit connection, a friction-fit connection, or adhesive.

The middle section 62 has an exposed outer surface 74 that is generally flush with the outer surface 38 of first electrical contact 20 and the outer surface 48 of housing 18. The outer surface 74 has a proximal end 76 that is adjacent the distal end 42 of the exposed outer surface 38 of the first electrical contact 20. The outer surface 74 has a distal end 78 that is adjacent the second electrical contact 24. The outer surface of proximal section 60 and the outer surface of distal section 64 are spaced radially inward from the outer surface 74 of middle section 62, as shown in FIG. 8. The proximal section 60 extends through the second opening 56 of the first electrical contact 20 and into the channel defined by the inner surface 50 of first electrical contact 20. The distal section 64 of the spacer 22 extends from the middle section 62 toward an end surface 80 of the second electrical contact 24. As shown in FIG. 8, an inner surface 82 of the spacer 22 defines a channel through the spacer 22 with a first opening 84 and a second opening 86 at the distal section 64.

Referring to FIG. 6, the second electrical contact 24 is coupled to and extends outward from the spacer 22. The second electrical contact 24 has an exposed side surface 88 that extends generally perpendicular from and is formed integrally with end surface 80. The exposed side surface 88 is cylindrical and extends in a continuous loop around the base 14. The exposed side surface 88 has a proximal end 90 that is adjacent the distal end 78 of the outer surface 74 of the spacer 22. The exposed side surface 88 has a distal end 92 adjacent the end surface 80. The end surface 80 of the second electrical contact 24 substantially blocks the second opening 86 at the distal section 64 of the spacer 22 to substantially enclose an interior cavity 94. The interior cavity 94 is positioned between portions of the housing 18, the first electrical contact 20, the spacer 22, and the second electrical contact 24. The second electrical contact 24 is formed from an electrically conductive material with both the side surface 88 and end surface 80 being electrically conductive. The side surface 88 of the second electrical contact 24 is generally flush with the outer surface 74 of spacer 22, the outer surface 38 of first electrical contact 20, and the outer surface 48 of housing 18. A post 96 extends upward from end surface 80 into the interior cavity 94. A electrical conductor (not shown) may electrically connect the post 96 to a circuit board 100 and/or to an electrical terminal of battery 26.

The first electrical contact 20, spacer 22, and second electrical contact 24 may be assembled with housing 18 by first inserting first electrical contact 20 into housing 18. The first electrical contact 20 may be joined to housing 18 in any of the manners described above. The proximal section 60 of spacer 22 may next be inserted into first electrical contact 20 until the clips 66 engage first electrical contact 20. The second electrical contact 24 may then be pressed over the distal section 64 of spacer 22 until the clips 68 on spacer 22 engage the second electrical contact 24.

A light source 98 is positioned in the interior cavity 94. The light source 98 may be any type of light source (e.g., an LED, incandescent, halogen, or fluorescent light) capable of emitting light so that it is visible from an exterior of the vaporizer 12. The spacer 22 may be translucent or transparent so that light emitted from the light source 98 is visible at the outer surface 74 of the spacer 22. An electrical conductor (not shown) may electrically connect the light source 98 to the circuit board 100, or the light source 98 may be mounted directly on the circuit board 100 and receive power from the circuit board 100 via a connection between the battery 26 and circuit board 100.

Battery 26 is electrically coupled to the first electrical contact 20 and to the second electrical contact 24 for charging battery 26 via an external power source in contact with first and second electrical contacts 20, 24. Battery 26 may be directly coupled to first electrical contact 20 and to second electrical contact 24 via an electrical conductor (not shown) that extends from a positive terminal of battery 26 to one of electrical contacts 20, 24 and another electrical conductor that extends from a negative terminal of battery 26 to the other of electrical contacts 20, 24. The positive and negative terminals of battery 26 may also be electrically connected to circuit board 100, which in turn is electrically connected to each of first electrical contact 20 and second electrical contact 24. The circuit board 100 may include a battery protection circuit to protect battery 26 from overcharging or other undesirable conditions. Battery 26 may be any type of suitable battery for storing and providing electrical power to a heater of cartridge 16. For example, battery 26 may be nickel cadmium (NiCd), nickel-metal hydride (NiMH), lithium ion (Li-ion), lithium ion polymer (Li-ion polymer), or rechargeable alkaline. Battery 26 is further electrically coupled to electromechanical connector 36, either directly or through circuit board 100, for providing electrical power to cartridge 16.

Circuit board 100 is electrically coupled to battery 26, a sensor 102, and light source 98. Circuit board 100 may further be electrically coupled to electromechanical connector 36 and first and second electrical contacts 20 and 24 as described above. Circuit board 100 may include a controller that receives a signal from sensor 102 and activates light source 98 based on the signal. The sensor 102 may be a pressure sensor or air flow sensor that detects when a user draws air through cartridge 16 during use of vaporizer 12. When the sensor 102 detects air drawn through cartridge 16, the controller may electrically couple battery 26 to electromechanical connector 36 for powering a heater of cartridge 16 and vaporizing a payload within the cartridge 16. When the sensor 102 detects air drawn through cartridge 16, the controller may also turn on light source 98. The sensor 102 is in fluid communication with the cartridge through the air flow path 106 shown in FIG. 5. The sensor 102 is positioned in a seal 104 that sealingly engages the inner surface 46 of the housing 18.

The controller further may be electrically coupled to a sensor (e.g., a temperature, pressure, or air flow sensor) that detects a condition of vaporizer 12 and alters the level of power provided through electromechanical connector 36 to cartridge 16 based on the sensed condition. For example, a temperature sensor may sense the temperature of fluid payload and/or vaporized payload within cartridge 16 and/or the temperature of a heater of cartridge 16, and the controller may raise or lower the level of power provided to cartridge 16 based on the sensed temperature. Likewise, a pressure and/or air flow sensor may sense the pressure or air flow rate of air within cartridge 16, and the controller may raise or lower the level of power provided to cartridge 16 based on the sensed pressure and/or air flow rate. The controller may cause electrical power to be provided to electromechanical connector 36 when a user activates a user input device, such as a button, of vaporizer 12. The controller may store information regarding vaporizer 12 (e.g., the charge level of battery 26, the amount of time vaporizer 12 and/or cartridge 16 have been used to vaporize a fluid payload, a level of a fluid payload remaining within cartridge 16, and/or the amount or dose of payload provided to a user during a particular session of vaping with vaporizer 12) and transmit the information to an external device, such as a mobile device or computer, through a wireless transmitter or transceiver.

As shown in FIG. 5, electromechanical connector 36 is joined to the second end 30 of housing 18. The electromechanical connector 36 enables the transmission of electrical power from the base 14 to the cartridge 16 and also physically joins the base 14 and cartridge 16 in a releasable manner. The electromechanical connector 36 provides an electrical interface that includes two conductors, a central pin 108 and an outer ring 110. The central pin 108 may be electrically connected to the positive terminal of battery 26 and the outer ring 110 may be electrically connected to the negative terminal of battery 26, or vice versa. The electromechanical connector 36 includes female threads designed to engage male threads of an electromechanical connector (not shown) of cartridge 16. For example, in a common implementation, the electromechanical connectors comprise M7×0.5 mm threaded connectors which are commonly referred to as "510 threaded connectors." The first connector (i.e., the connector on base 14) comprises a female 510 threaded connector and the second connector (i.e., the connector on cartridge 16) comprises a male 510 threaded connector. Of course, the invention is not limited to the use of 510 threaded connectors and other types of two-conductor connectors may also be used. For example, the mechanical connection between base 14 and cartridge 16 may comprise a threaded connection, a pressure or friction fit connection, a twist mechanical lock, a magnetic connection, or any other mechanical connecting means known to those skilled in the art.

Referring to FIG. 1, the cartridge 16 includes a payload reservoir 112 configured to contain a fluid payload for vaporization. A heater 114 is in fluid communication with the payload reservoir 112. The heater 114 is electrically connected to the electromechanical connector (not shown) of the cartridge 16 for receiving the electrical power from the controller of the base 14. The heater 114 is configured to heat the payload until it vaporizes when receiving the electrical power. A user may draw the vaporized payload through an outlet 116 of the cartridge 16. The outlet 116 is in fluid communication with the sensor 102 through a channel in cartridge 16 that is in fluid communication with the air flow path 106 shown in FIG. 5.

Figure 10:
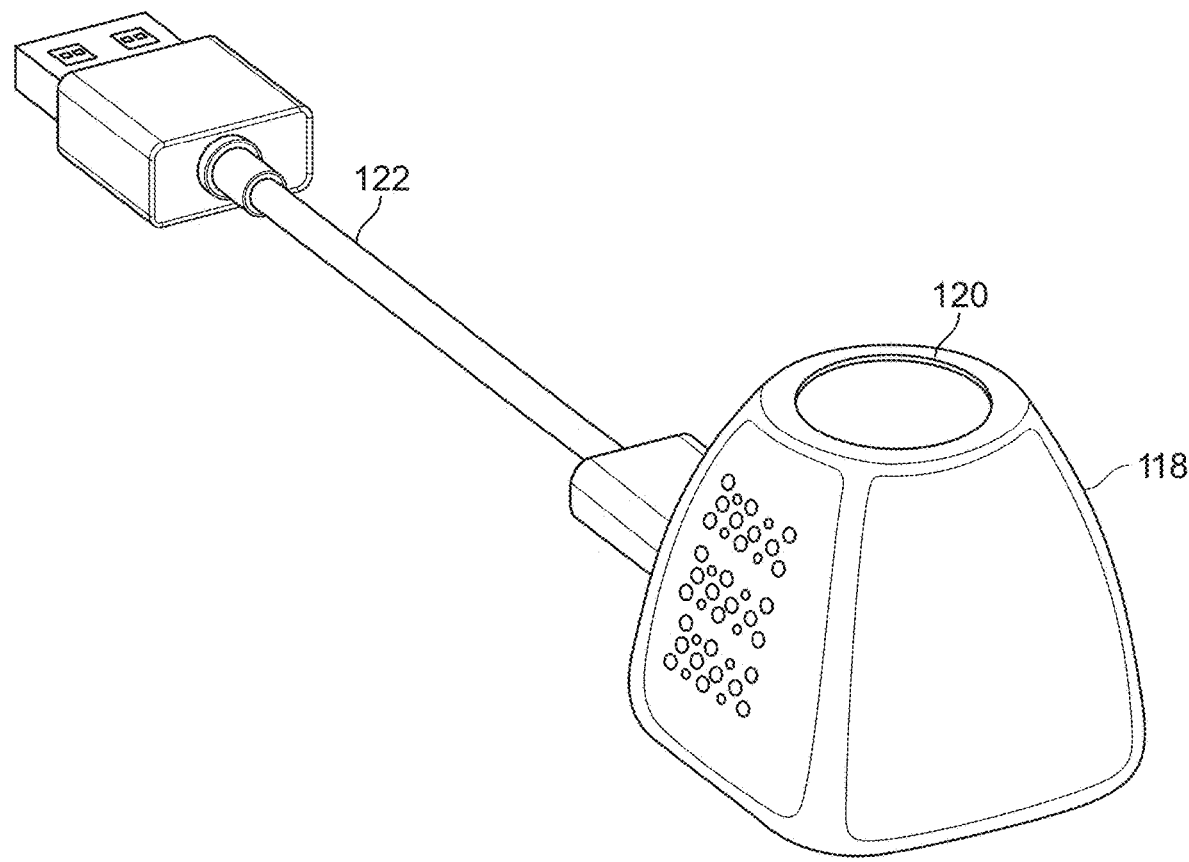
FIG. 10 is a perspective view of a charger for use with the charging structure shown in FIG. 3.

Referring to FIG. 10, a charger 118 is configured for charging battery 26. Charger 118 includes a receptacle 120 that is configured for receiving the end of vaporizer 12 including the charging structure 10. The charger 118 includes two electrical contacts that are spaced apart in the same manner as the first and second electrical contacts 20 and 24 of charging structure 10. Thus, when the charging structure 10 is inserted in the receptacle 120, each electrical contact of the charger 118 is electrically connected to one of the first and second electrical contacts 20, 24. The charger 118 includes a charging cable 122 for connecting the charger 118 to a power source. The charging cable 122 may include a connector that is removably received by a charging port on the charger 118, or the charging cable 122 may be permanently connected to the rest of the charger 118. The charging cable 122 may be any suitable type of electrical cable. For example, charging cable 122 may have a USB type A, B, mini A, mini B, micro A, micro B, or C connector, a Lightning connector, a coaxial power connector, or any other type of connector suitable for connection both to an external power source and to the charger 118. The charger 118 may also include a charging port that is configured for coupling with any of the types of connectors listed above. The charger 118 may include a circuit board with a controller that is programmed with battery charging logic to charge battery 26 in a particular manner depending on the storage capacity of battery 26, the charge state of battery 26, and the level of power input to the charger 118 from an external source.

In use, when battery 26 is charged, a user may connect cartridge 16 to base 14 and draw air through outlet 116. Sensor 102 senses that air is being drawn through outlet 116 and the controller of base 14 sends electrical power from battery 26 to the heater 114 of cartridge 16 through electromechanical connector 36. The heater 114 heats the payload within cartridge 16, and the user draws the vaporized payload through the outlet 116 of cartridge 16. The controller of base 14 further activates the light source 98 as the user draws air and vaporized payload through the cartridge 16. The light source 98 may animate with a breathing effect (e.g., the light source 98 gradually increases and then decreases in intensity) to show that the vaporizer 12 is operating properly. When the charge of battery 26 decreases below a certain level, the controller of base 14 may cause light source 98 to flash one or more times as an indication to the user that the battery 26 needs to be recharged. To recharge the battery 26, the user inserts the charging structure 10 into the receptacle 120 of the charger 118 and connects the charging cable 122 to an external source of power. A light on the charger 118 may indicate both when the battery 26 of base 14 is actively being charged (e.g., the light may gradually increase and then decrease in intensity) and when the battery 26 is fully recharged and ready for use (e.g., the light may remain on at a constant intensity). The cartridge 16 does not need to be disconnected from the base 14 while the battery 26 is being recharged.

In an alternative embodiment, charging structure 10 may be configured so that the first electrical contact 20 is positioned at the second end 30 of the housing 18 while the second electrical contact 24 is positioned at the first end 28 of the housing 18. In such a configuration, housing 18 and spacer 22 may be configured so that spacer 22 attaches to the first end 28 of housing 18 (e.g., a slot may be formed in the inner surface 46 of the housing 18 to receive the clips 66 of spacer 22. Further, spacer 22 may be omitted, and second electrical contact 24 and housing 18 may be configured so that second electrical contact 24 attaches to the first end 28 of housing 18. The second end 30 of the housing 18 and first electrical contact 20 may be configured so that first electrical contact 20 attaches to the second end 30 of the housing 18 (e.g., a recess may be formed in the housing 18 at second end 30 sized for receiving first electrical contact 20). The charger 118 may further be configured to have electrical contacts that are configured for making contact with the first electrical contact 20 at the second end 30 of housing 18 and the second electrical contact 24 at the first end 28 of housing 18.

Figure 11:
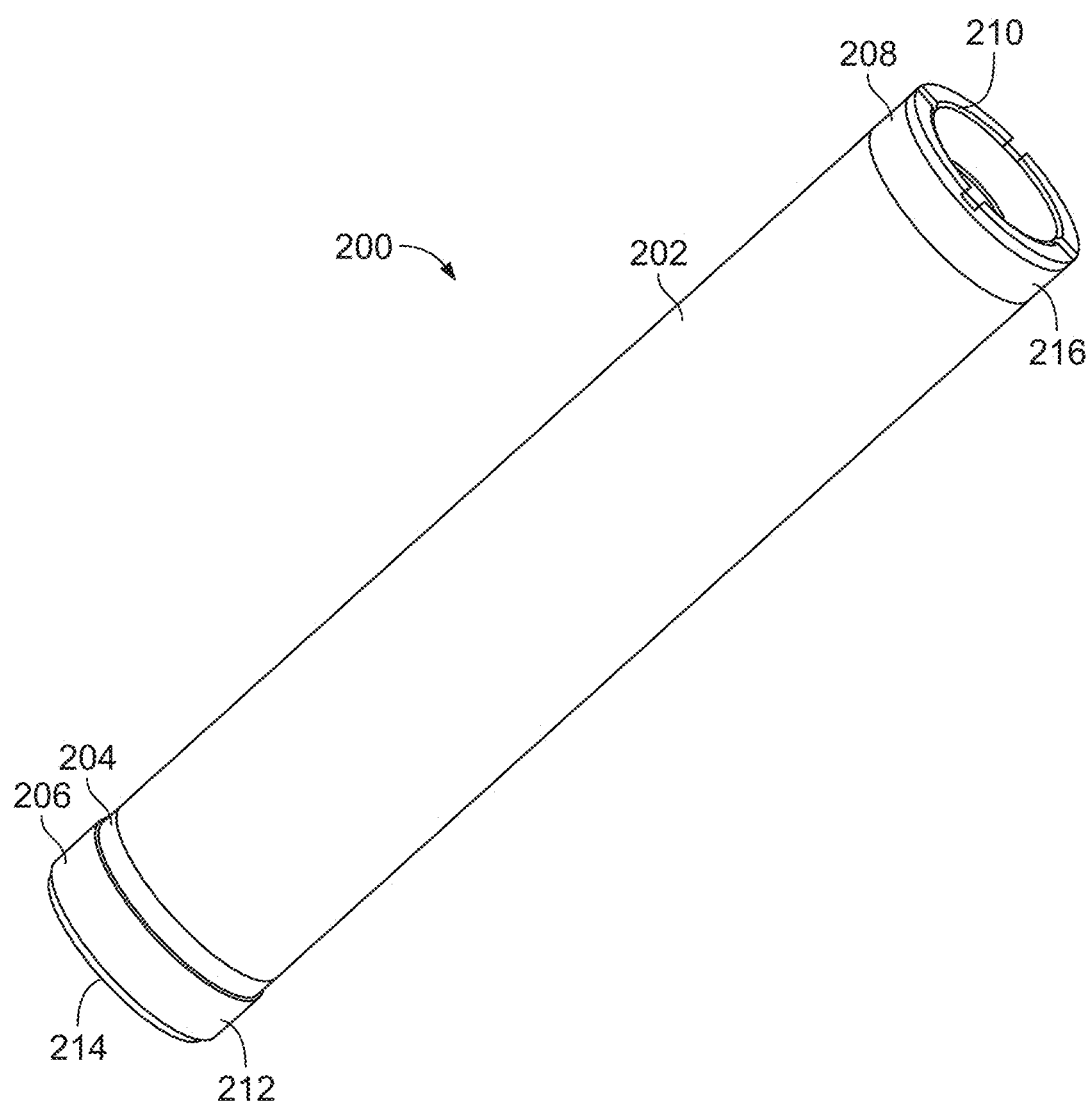
FIG. 11 is a perspective view of a base of a vaporizer having an alternative embodiment of charging structure in accordance with the invention described herein.

For example, FIG. 11 shows an alternative embodiment of charging structure 200 that includes a housing 202, a spacer 204, a first electrical contact 206, and a second electrical contact 208. The spacer 204 is joined to a first end of the housing 202 and the first electrical contact 206 is joined to the spacer 204. The spacer 204 may be joined to the housing 202 in a similar manner as described above with respect to first electrical contact 20 and housing 18. Further, the first electrical contact 206 may be joined to spacer 204 in a similar manner as described above with respect to second electrical contact 24 and spacer 22. The second electrical contact 208 is joined to a second end of the housing 202. The second electrical contact 208 may be joined to the housing 202 in a similar manner as described above with respect to first electrical contact 20 and housing 18. An electromechanical connector 210 is joined to the second electrical contact 208. The electromechanical connector 210 may be similar to the electromechanical connector 36 described above. The first electrical contact 206 has an electrically conductive side surface 212 extending in a continuous loop and electrically conductive end surface 214 in a similar manner as the second electrical contact 24 described above. The second electrical contact 208 has an electrically conductive outer surface 216 extending in a continuous loop in a similar manner as the first electrical contact 20 described above. The first electrical contact 206 may have substantially the same structure as the second electrical contact 24 described above, and the second electrical contact 208 may have substantially the same structure as the first electrical contact 20 described above. The charging structure 200 may have a battery, light source, circuit board, and sensor configured in a similar manner as described above for charging structure 10. The charging structure 200 may further operate in a similar manner as described above for charging structure 10.

In another alternative embodiment, charging structure 10 may be configured so that the housing 18 serves as the first electrical contact such that the first electrical contact 20 shown in the drawings is not needed. In such a configuration, housing 18 and spacer 22 may be configured so that spacer 22 attaches to the first end 28 of housing 18 (e.g., a slot may be formed in the inner surface 46 of the housing 18 to receive the clips 66 of spacer 22. The housing 18 is formed from an electrically conductive material and may be electrically connected to the battery 26 or circuit board 100 as described above in connection with first electrical contact 20. The charger 118 may further be configured to have electrical contacts that are configured for making contact with the housing 18 itself and the second electrical contact 24 at the first end 28 of housing 18.

Figure 12:
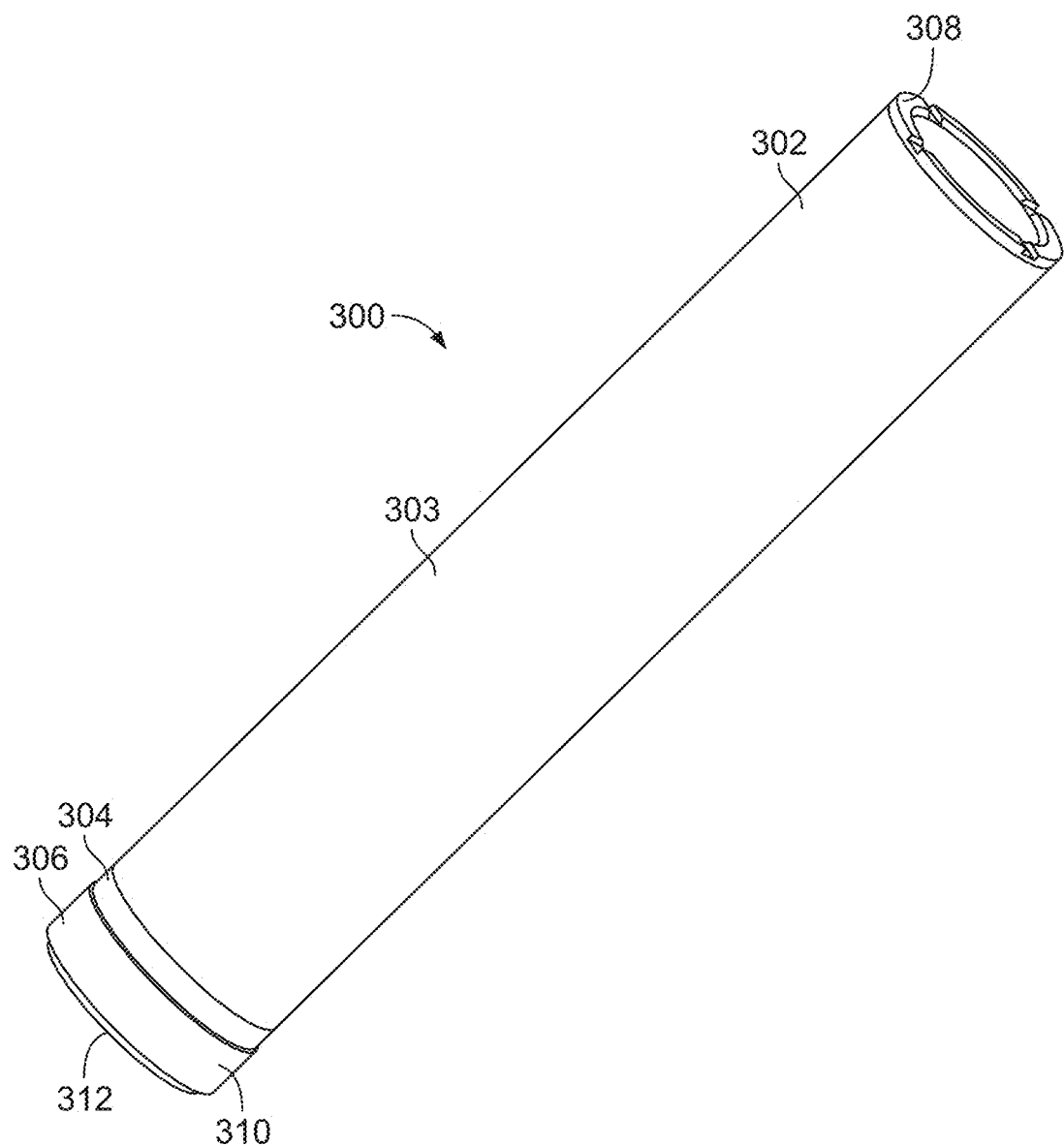
FIG. 12 is a perspective view of another base of a vaporizer having an alternative embodiment of charging structure in accordance with the invention described herein.

For example, FIG. 12 shows an alternative embodiment of charging structure 300 that includes a housing 302 with an electrically conductive outer surface 303 that serves as a first electrical contact, a spacer 304, and a second electrical contact 306. The spacer 304 is joined to a first end of the housing 302 and the second electrical contact 306 is joined to the spacer 304. The spacer 304 may be joined to the housing 302 in a similar manner as described above with respect to first electrical contact 20 and housing 18. Further, the second electrical contact 306 may be joined to spacer 304 in a similar manner as described above with respect to second electrical contact 24 and spacer 22. An electromechanical connector 308 is joined to a second end of the housing 302. The electromechanical connector 308 may be similar to the electromechanical connector 36 described above. The electrically conductive outer surface 303 of the housing 302 extends in a continuous loop in a similar manner as the first electrical contact 20 described above. The second electrical contact 306 has an electrically conductive side surface 310 extending in a continuous loop and electrically conductive end surface 312 in a similar manner as the second electrical contact 24 described above. The second electrical contact 306 may have substantially the same structure as the second electrical contact 24 described above. The charging structure 300 may have a battery, light source, circuit board, and sensor configured in a similar manner as described above for charging structure 10. The charging structure 300 may further operate in a similar manner as described above for charging structure 10.

From the foregoing it will be seen that this invention is one well adapted to attain all ends and objectives hereinabove set forth, together with the other advantages which are obvious and which are inherent to the invention.

Since many possible embodiments may be made of the invention without departing from the scope thereof, it is to be understood that all matters herein set forth or shown in the accompanying drawings are to be interpreted as illustrative, and not in a limiting sense.

While specific embodiments have been shown and discussed, various modifications may of course be made, and the invention is not limited to the specific forms or arrangement of parts and steps described herein, except insofar as such limitations are included in the following claims. Further, it will be understood that certain features and subcombinations are of utility and may be employed without reference to other features and subcombinations. This is contemplated by and is within the scope of the claims.

What is claimed and desired to be secured by Letters Patent is as follows:

1. A vaporizer comprising:
    a base comprising:
        a housing comprising first and second ends;
        a first electrical contact coupled to and extending outward from the first end of the housing, wherein the first electrical contact comprises an exposed outer surface that extends in a continuous loop;
        a spacer coupled to the first electrical contact; and
        a second electrical contact coupled to and extending outward from the spacer, wherein the second electrical contact comprises an exposed side surface that extends in a continuous loop, wherein the second electrical contact comprises an end surface coupled to the side surface, wherein both the side surface and the end surface are electrically conductive, and wherein the end surface of the second electrical contact is exposed; and
    a cartridge that is configured for connection to the base adjacent the second end of the housing, the cartridge defining an outlet, and the cartridge being configured so that a vaporized payload may be drawn through the outlet.

2. The vaporizer of claim 1, further comprising a light source positioned in an interior cavity defined by at least one of the housing, the first electrical contact, the spacer, or the second electrical contact.

3. The vaporizer of claim 2, wherein the spacer is translucent or transparent, and wherein the light source is positioned so that light emitted from the light source is visible at an outer surface of the spacer.

4. The vaporizer of claim 1, wherein the exposed outer surface of the first electrical contact and the exposed side surface of the second electrical contact are each cylindrical.

5. The vaporizer of claim 1, wherein the exposed side surface of the second electrical contact is integrally formed with the end surface.

6. The vaporizer of claim 1, wherein the first electrical contact comprises a coupling section that engages an inner surface of the housing, wherein the spacer comprises a proximal section that engages an inner surface of the first electrical contact, and wherein the spacer comprises a distal section that engages an inner surface of the second electrical contact.

7. The vaporizer of claim 1, wherein the exposed outer surface of the first electrical contact comprises a proximal end adjacent the first end of the housing and a distal end, wherein the spacer comprises a second exposed outer surface with a proximal end adjacent the distal end of the exposed outer surface of the first electrical contact and a distal end, and wherein the exposed side surface of the second electrical contact comprises a proximal end adjacent the distal end of the second exposed outer surface of the spacer and a distal end.

8. The vaporizer of claim 7, wherein the exposed outer surface of the first electrical contact, the second exposed outer surface of the spacer, and the exposed side surface of the second electrical contact are substantially flush with an outer surface of the housing.

9. The vaporizer of claim 7, wherein the housing defines an opening at the first end, and wherein the first electrical contact comprises a coupling section that extends from the proximal end of the exposed outer surface through the opening.

10. The vaporizer of claim 9, wherein the first electrical contact defines a second opening at the distal end of the first electrical contact, wherein the spacer comprises a proximal section that extends from the proximal end of the second exposed outer surface through the second opening, and wherein the spacer comprises a distal section that extends from the distal end of the second exposed outer surface toward the end surface of the second electrical contact.

11. The vaporizer of claim 10, wherein the distal section of the spacer defines a third opening, and wherein the end surface of the second electrical contact substantially blocks the third opening.

12. The vaporizer of claim 10, wherein the proximal section of the spacer engages a first inner surface of the first electrical contact, and wherein the distal section of the spacer engages a second inner surface of the second electrical contact.

13. The vaporizer of claim 1, wherein the first electrical contact comprises a coupling section extending from the exposed outer surface, wherein the coupling section engages an inner surface of the housing.

14. The vaporizer of claim 13, wherein the housing defines an opening at the first end, and wherein the coupling section extends through the opening.

15. The vaporizer of claim 13, wherein the coupling section is joined to the housing by at least one of a press-fit connection, a friction-fit connection, adhesive, brazing, or welding.

16. The vaporizer of claim 1, wherein the spacer comprises a proximal section that engages an inner surface of the first electrical contact, and wherein the spacer comprises a distal section that engages the second electrical contact.

17. The vaporizer of claim 16, wherein the proximal section of the spacer engages the inner surface of the first electrical contact by at least one of a press-fit connection, a friction-fit connection, or adhesive.

18. The vaporizer of claim 1, wherein the spacer is formed from an electrically insulating material.

19. The vaporizer of claim 1, further comprising a battery that is electrically coupled to the first electrical contact and to the second electrical contact.

20. The vaporizer of claim 19, further comprising an electromechanical connector positioned at the second end of the housing, the electromechanical connector comprising a positive electrical terminal that is electrically coupled to the battery and a negative electrical terminal that is electrically coupled to the battery.

21. The vaporizer of claim 1, wherein the cartridge contains a fluid payload.

* * * * *